United States Patent
Ohno (10) Patent No.: US 12,140,743 B2
(45) Date of Patent: Nov. 12, 2024

(54) MICROFLUIDIC DEVICE OBSERVATION DEVICE AND MICROFLUIDIC DEVICE OBSERVATION METHOD

(71) Applicant: Shimadzu Corporation, Kyoto (JP)

(72) Inventor: Yoshinori Ohno, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 754 days.

(21) Appl. No.: 17/262,144

(22) PCT Filed: Jul. 23, 2018

(86) PCT No.: PCT/JP2018/027554
§ 371 (c)(1),
(2) Date: Jan. 21, 2021

(87) PCT Pub. No.: WO2020/021604
PCT Pub. Date: Jan. 30, 2020

(65) Prior Publication Data
US 2021/0260582 A1    Aug. 26, 2021

(51) Int. Cl.
*G02B 21/00*    (2006.01)
*B01L 3/00*    (2006.01)
(Continued)

(52) U.S. Cl.
CPC .... *G02B 21/0056* (2013.01); *B01L 3/502715* (2013.01); *B01L 3/502761* (2013.01);
(Continued)

(58) Field of Classification Search
CPC .. G02B 21/0056; G02B 21/06; G06V 10/443; G06V 10/60; G06V 10/158;
(Continued)

(56) References Cited

U.S. PATENT DOCUMENTS

2011/0285837 A1* 11/2011 Bello ............... G06T 7/12
382/133
2013/0010108 A1* 1/2013 Hashizume ........ G01N 21/6428
348/135
(Continued)

FOREIGN PATENT DOCUMENTS

EP    2572205 A1    3/2013
JP    H07-078997 A    3/1995
(Continued)

OTHER PUBLICATIONS

First Office Action dated Dec. 26, 2023 for corresponding Chinese Patent Application No. 201880095672.1.
(Continued)

*Primary Examiner* — Khai M Nguyen
(74) *Attorney, Agent, or Firm* — Muir Patent Law, PLLC (57) ABSTRACT

A microfluidic-device observation apparatus 1 for observing a specimen present in a plurality of flow paths 103a to 103e arranged in a microfluidic device 100 is provided with: an imaging unit 4 configured to acquire an image of the microfluidic device 100; an extraction pixel selection unit 21 configured to select extraction pixels from a plurality of pixels by a certain criterion based on luminance values of the plurality of pixels constituting the acquired image; a flow path identification unit 22 configured to locate the plurality of flow paths 103a to 103e included in the image; a specimen-featured-pixels detection unit 24 configured to detect a certain number or more of extraction pixels consecutively present inside of the identified plurality of flow paths 103a to 103e as a specimen-featured-pixels group; and a statistical feature value calculation unit 26 configured to calculate a statistical feature value of the specimen based on the number of specimen-featured-pixels group and/or the
(Continued)

number of the extraction pixels constituting each of the specimen-featured-pixels group.

9 Claims, 8 Drawing Sheets

(51) Int. Cl.

| | | |
|---|---|---|
| *C12M 1/34* | (2006.01) | |
| *C12M 3/06* | (2006.01) | |
| *C12Q 1/04* | (2006.01) | |
| *G01N 15/14* | (2006.01) | |
| *G01N 15/1433* | (2024.01) | |
| *G02B 21/06* | (2006.01) | |
| *G06V 10/44* | (2022.01) | |
| *G06V 10/60* | (2022.01) | |
| *G06V 10/75* | (2022.01) | |

(52) U.S. Cl.
CPC .............. *C12M 1/34* (2013.01); *C12M 23/16* (2013.01); *C12Q 1/04* (2013.01); *G01N 15/1433* (2024.01); *G01N 15/1459* (2013.01); *G02B 21/06* (2013.01); *G06V 10/443* (2022.01); *G06V 10/60* (2022.01); *G06V 10/758* (2022.01); *G01N 2015/1486* (2013.01); *G01N 2015/1497* (2013.01)

(58) Field of Classification Search
CPC ........... G01N 15/1433; G01N 15/1459; G01N 2015/1486; G01N 2015/1497; B01L 3/502715; B01L 3/502761; C12M 1/34; C12M 23/16; C12Q 1/04
See application file for complete search history.

(56) References Cited

U.S. PATENT DOCUMENTS

| | | | |
|---|---|---|---|
| 2014/0349333 A1 | 11/2014 | Matsumoto et al. | |
| 2016/0160169 A1* | 6/2016 | Paczkowski | C12Q 1/00 |
| | | | 506/10 |
| 2018/0105855 A1* | 4/2018 | Paczkowski | B01L 3/5085 |
| 2020/0032196 A1* | 1/2020 | Tabata | G01N 1/40 |

FOREIGN PATENT DOCUMENTS

| | | | |
|---|---|---|---|
| JP | H09-140397 A | | 6/1997 |
| JP | H11-097512 A | | 4/1999 |
| JP | 2013-003011 A | | 1/2013 |
| JP | 2013-526717 A | | 6/2013 |
| JP | 2014-515128 A | | 6/2014 |
| JP | 2015-177806 A | | 10/2015 |
| JP | 2016-508034 A | | 3/2016 |
| JP | 2016-123366 A | | 7/2016 |
| JP | 2017184737 A | * | 10/2017 |
| WO | 2011/117952 A1 | | 9/2011 |
| WO | 2011/146006 A1 | | 11/2011 |
| WO | 2012/119191 A1 | | 9/2012 |
| WO | 2014/099643 A1 | | 6/2014 |

OTHER PUBLICATIONS

Written Opinion of the International Searching Authority (ISA237) for PCT application No. PCT/JP2018/027554 dated Sep. 25, 2018, submitted with a machine translation.
First Japanese Office Action dated Sep. 14, 2021 for the corresponding Japanese Patent Application No. 2020-531848, with a machine translation.
Second Office Action dated Jul. 29, 2024 issued for the corresponding Chinese Patent Application No. 201880095672.1.

* cited by examiner

MICROFLUIDIC DEVICE OBSERVATION DEVICE AND MICROFLUIDIC DEVICE OBSERVATION METHOD

TECHNICAL FIELD

The present invention relates to a microfluidic-device observation apparatus and a microfluidic-device observation method for observing a specimen present in flow paths of a microfluidic device in which one or a plurality of flow paths is arranged.

BACKGROUND ART

A microfluidic device is a device in which one or a plurality of flow paths is formed in a substrate by a micromachining technique using a micro electro mechanical system (MEMS: Micro Electro Mechanical System) or the like (see, for example, Patent Document 1). The microfluidic device is produced by, for example, bonding an upper substrate in which concave portions serving as flow paths are formed on the lower surface and a through-hole used for introducing a fluid to be examined is formed at a position corresponding to an end portion of the flow path and a lower substrate. The microfluidic device is used to test the susceptibility of bacteria or fungi (target bacteria) to an antimicrobial agent, for example, as described in Patent Document 2.

PRIOR ART DOCUMENT

Patent Document

Patent Document 1: Japanese Unexamined Patent Application Publication No. 2013-3011
Patent Document 2: Japanese Unexamined Patent Application Publication No. 2015-177806
Patent Document 3: Japanese Unexamined Patent Application Publication No. H11-97512

SUMMARY OF THE INVENTION

Problems to be Solved by the Invention

Figure 1:
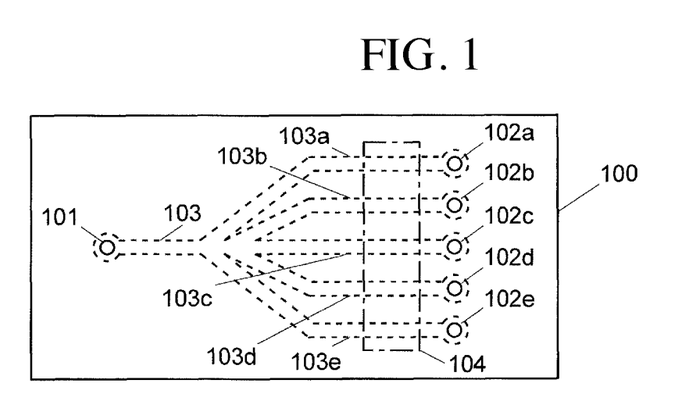
FIG. 1 is a configuration example of a microfluidic device.

In order to specifically explain the problems to be solved by the present invention, an exemplary microfluidic device used in the examination will be described (see FIG. 1). One inlet port 101 and five air ports 102a to 102e are provided on the upper surface of a microfluidic device 100. Inside the microfluidic device 100, a bacterial suspension introduction flow path 103 having one end directly below the inlet port 101 is provided. The bacterial suspension introduction flow path 103 branches in the middle into five branched flow paths 103a to 103e, and the branched flow paths extend to just below the air ports 102a to 102e, respectively. The five branched flow paths 103a to 103e are arranged parallel to each other in the vicinity of the air ports 102a to 102e.

In the examination of the target bacteria using the microfluidic device 100, first, antimicrobial solutions a to d containing the same kind of an antimicrobial agent different in the concentration are introduced from the air ports 102a to 102d into the branched flow paths 103a to 103d. The amounts of the antimicrobial solutions a to d introduced here are such that the antimicrobial solutions stay inside the branched flow paths 103a to 103d (do not reach the bacterial suspension introduction flow path 103). No antimicrobial solution is introduced into the branched flow path 103e.

Then, the antimicrobial solutions a to d introduced into the branched flow paths 103a to 103d are dried so that the antimicrobial agents are fixed to the wall surfaces of the branched flow paths 103a to 103d. Subsequently, a bacterial solution containing target bacteria is introduced into the bacterial suspension introduction flow path 103 through the inlet port 101. The air ports 102a to 102e for ventilation are formed at the ends of the branched flow paths 103a to 103e. Therefore, the air in each of the branched flow paths 103a to 103e is discharged from the air ports in accordance with the inflow of the bacterial suspension, and the bacterial suspension flows into each of the branched flow paths 103a to 103e. In the branched flow paths 103a to 103d, the inflowed bacterial suspension comes into contact with the antimicrobial agent fixed to the wall surface of each flow path.

After a predetermined time has elapsed since the introduction of the bacterial suspension, the microfluidic device 100 is set at a predetermined position of a microscope, and the image of an area (observation area) 104 in the visual field of the microscope is acquired. Then, portions corresponding to the respective branched flow paths 103a to 103e are identified from the image of the observation area 104, and the states of the target bacteria present in the branched flow paths 103a to 103e are confirmed.

As described above, since the antimicrobial solution is not introduced into one of the branched flow paths (in the above-described example, the branched flow path 103e), by comparing the number and the shape of bacteria confirmed from the image of the branched flow path 103e with the number and the shape of bacteria confirmed from the other images of the branched flow paths 103a to 103d, it is possible to know the effect on the target bacteria can be obtained by using how much concentration of the antimicrobial solution containing the antimicrobial agent.

In the above-described examination, it is common to repeatedly perform an operation of observing the state of the target bacteria by causing the target bacteria to act on the antimicrobial agent for a predetermined time to confirm the state change of the target bacteria with the lapse of time. Therefore, every time the examiner observes the microfluidic device with a microscope, it is necessary to repeat the operation of counting the number of the target bacteria present in the flow paths and checking the shape of the target bacteria, which is laborious. Further, in many cases, the examinations are performed by using a large number of microfluidic devices. Therefore, it is necessary to image each of the microfluidic devices and count the number of the target bacteria present in the flow paths and check the shape of the target bacteria for each of the large number of microfluidic devices, which is a great burden on the examiner.

The object to be solved by the present invention to provide a microfluidic-device observation apparatus and a microfluidic-device observation method capable of easily grasping a state of a specimen present in flow paths provided in a microfluidic device.

Means for Solving the Problem

According to the first aspect of the present invention made to solve the above-described problems, a microfluidic-device observation apparatus for observing a specimen present in a plurality of flow paths arranged in a microfluidic device, includes:
  an imaging unit configured to acquire an image of the microfluidic device;

an extraction pixel selection unit configured to select extraction pixels from a plurality of pixels constituting the acquired image by a certain criterion based on luminance values of the plurality of pixels;

a flow path identification unit configured to locate the plurality of flow paths included in the image;

a specimen-featured-pixels detection unit configured to detect specimen-featured-pixels which have a certain number or more of extraction pixels consecutively present in the plurality of identified flow paths; and a statistical feature value calculation unit configured to calculate a statistical feature value of the specimen-featured-pixels group based on a number and/or a shape of the specimen-featured-pixels group.

The type of the imaging unit is not limited as long as it is capable of acquiring an image in which contrast appears at boundaries of the flow paths formed in the microfluidic device and at a position where the specimen is present. As the imaging unit, for example, an optical microscope, an optical camera, a phase contrast microscope, or a differential interferometric microscope can be used.

In the microfluidic-device observing apparatus according to the first aspect of the present invention, first, the microfluidic device is set at a predetermined position of the imaging unit so that an area in which the plurality of flow paths is arranged is in the field of view, and an image of the area is acquired. Subsequently, the extraction pixel selection unit selects extraction pixels from a plurality of pixels based on a predetermined criterion based on the luminance values of the plurality of pixels constituting the acquired image. This selection can be performed by, for example, using a luminance value (background luminance value) assumed for a pixel at a position where neither the boundary of the flow paths nor the specimen is present as a threshold value, and identifying pixels whose luminance value is higher (or lower) than the threshold value. Alternatively, the average value of the luminance values of all the pixels or the luminance value of the pixel at a position where neither the boundary of the flow paths nor the specimen is considered to be present, such as, e.g., the four corners of the image, may be set as a threshold value, and pixels having a luminance value higher than (or lower than) the threshold value may be identified. Further, instead of using a luminance value itself, the edge intensity (the amount of change in luminance value) may be obtained from the image data using a differential filter, and extraction pixels may be selected based on the result of comparing the edge intensity with a predetermined value. By using such a differential filter, it is possible to remove the background to easily select extraction pixels corresponding to the boundary of the flow paths and the specimens in the flow paths. Whether to select a pixel having a high luminance value or a pixel having a low luminance value may be determined in accordance with the characteristics of the imaging unit to be used (i.e., whether the boundary of the flow paths or the specimen appears bright or dark).

Next, the flow path identification unit identifies the positions of the plurality of flow paths included in the image of the microfluidic device acquired by the imaging unit. This can be done, for example, by performing template matching in which a template image of a microfluidic device to be used is prepared and the image acquired by the imaging unit is collated with the template image. In this process, the positions of the flow paths may be identified by collating the image itself of the microfluidic device with the template image, or the positions of the flow paths may be identified by collating the positions of extraction pixels selected by the extraction pixel selection unit with the template image. Further, in cases where the microfluidic device has a plurality of flow paths having the same width arranged in parallel to each other in at least a part of the area, the positions of the plurality of flow paths can be identified by the image analysis processing such as explanatory processing to be described later.

In some cases, not only structures such as specimens (e.g., bacteria) but also noise-induced contrast may appear inside the flow paths identified by the flow path identification unit. Therefore, there is a possibility that pixels corresponding to the positions where they are present are mixed in the extraction pixels selected by the extraction pixel selection unit. Therefore, next, a certain number or more of extraction pixels consecutively present in the identified plurality of flow paths are detected as a specimen-featured-pixels group. The predetermined number may be the number of pixels corresponding to the smallest size assumed to be a specimen. Since noise data is rarely continuously present in a large number of pixels, the noise is removed by this processing.

Next, the statistical feature value calculation unit calculates the statistical feature value of the specimen-featured-pixels group based on the number and/or the shape of the specimen-featured-pixels group. The statistical feature value is an amount (value) related to the number and/or the shape of the specimen-featured-pixels group. The statistical feature value may include a feature value that does not directly depend on the shape of the specimen-featured-pixels group, such as, e.g., the area and the length of the specimen-featured-pixels group. The number of the specimen-featured-pixels group corresponds to the number of specimens present in the flow path. Further, the shape of the specimen-featured-pixels group, that is, the array of pixels constituting each specimen-featured-pixels group, corresponds to the shape of one specimen. When the microfluidic-device observation apparatus according to the present invention is used, an image acquired by the imaging unit is processed in order by the flow path identification unit, the extraction pixel selection unit, the specimen-featured-pixels detection unit, and the statistical feature value calculation unit, and a statistical feature value of the specimen present in the flow path is obtained. Therefore, it is unnecessary for the examiner to count the number or confirm the shape of the specimen present in the flow path, so that the state of the specimen can be easily grasped.

In the microfluidic-device observation apparatus according to the first aspect of the present invention, the statistical feature value calculation unit calculates a representative value of the statistical feature values of the plurality of specimen-featured-pixels groups in a case where a plurality of specimen-featured-pixels groups is present in one flow path. The representative value of the statistical feature value may be suitably selected from the group consisting of a mean value, a median value, a mode value, and a combination thereof. By using a microfluidic-device observation apparatus of this aspect, it is possible to easily know, for example, the mean size and shape of a specimen present in each flow path.

When the specimen is a biological sample, such as, e.g., a cell and a bacterium, the microfluidic-device observation apparatus according to the first aspect of the present invention further includes:

a determination unit configured to determine a state of the specimen based on a result of comparing the statistical feature value determined for one of the plurality of flow paths with the statistical feature value determined for the other flow paths.

When the susceptibility of a specimen, such as, e.g., a cell and a bacterium, to an agent, such as, e.g., an antimicrobial agent, is examined, in general, an agent is not introduced into one of a plurality of flow paths, and the number and/or the shape of the specimen present in the flow path is used as a criterion for determining a specimen condition. When the specimen is a biological sample, the condition can be easily known by using a microfluidic-device observation apparatus of this embodiment. When a plurality of specimen-featured-pixels groups is present in one flow path, the state of the specimen may be determined based on the representative value of the statistical feature values.

According to the second aspect of the present invention made to solve the above-described problems, a microfluidic-device observation apparatus for observing a specimen present in a plurality of flow paths arranged in a microfluidic device, comprising:

an imaging unit configured to acquire an image of the microfluidic device;
a flow path identification unit configured to locate the plurality of flow paths included in the image; and
an identification unit configured to identify a number and/or a shape of the specimen present in each of the plurality of identified flow paths when the acquired image is input.

In the microfluidic-device observation apparatus of the second aspect of the present invention, instead of the extraction pixel selection unit, the specimen-featured-pixels detection unit, and the statistical feature value calculation unit of the first aspect of the present invention, an identification unit is used in which when an image of the microfluidic device image acquired by the imaging unit is input, the number and/or the shape of the specimen included in each of the plurality of flow paths identified by the flow path identification unit is identified. Also by using the microfluidic-device observation apparatus of this embodiment, the state of the specimen can be easily grasped in the same manner as in the first aspect of the present invention.

In a case where a specimen is a biological sample, such as, e.g., a cell and a fungi, in the microfluidic-device observation apparatus of the second aspect of the present invention, the identification unit may be configured such that a state of the specimen present in each flow path is determined based on the number and/or the shape of the identified specimen.

By using the microfluidic-device observation apparatus of this aspect of the present invention when the specimen is a biological sample, it is possible to easily know the state.

The microfluidic-device observational technique of the present invention can be suitably used to examine the sensitivity of a target bacteria to an agent.

In other words, according to the third aspect of the present invention made to solve the above-described problems, a microfluidic-device observation method for observing bacteria introduced together with an agent into a plurality of flow paths arranged in a microfluidic device, the method includes:

obtaining an image of a microfluidic device;
selecting extraction pixels from a plurality of pixels by a certain criterion based on luminance values of the plurality of pixels constituting the acquired image;
identifying positions of the plurality of flow paths included in the image;
detecting a prescribed number or more of extraction pixels consecutively present in the plurality of identified flow paths as a specimen-featured-pixels group; and obtaining a statistical feature value of the specimen-featured-pixels group based on the number and/or the shape of the specimen-featured-pixels group.

Further, according to the fourth aspect of the present invention made to solve the above-described problems, a microfluidic-device observation method for observing bacteria introduced together with an agent into a plurality of flow paths arranged in a microfluidic device, includes:

acquiring an image of the microfluidic device;
identifying positions of the plurality of flow paths included in the image; and
identifying a number and/or a shape of the bacteria present in the plurality of identified flow paths according to an input of the acquired image.

Effects of the Invention

By using the microfluidic-device observation apparatus according to the first aspect or the second aspect of the present invention, or by using the microfluidic-device observation method according to the third aspect or the fourth aspect of the present invention, it is possible to easily grasp the state of a specimen present in the flow paths arranged in the microfluidic device.

EMBODIMENTS FOR CARRYING OUT THE INVENTION

Example 1 and 2 of a microfluidic-device observation apparatus according to the present invention will be described below with reference to the attached drawings. In these examples, by using a microfluidic device 100 described with reference to FIG. 1, the sensitivity of target bacteria to antimicrobial solutions a to d including the same antimicrobial agent different in the concentration from each other is examined. In this example, four antimicrobial solutions a to d different in the concentration are used in this example, but the number of the antimicrobial solutions (type of concentration) can be changed accordingly. In the case of using five or more types of antimicrobial solutions, a microfluidic device having six or more flow paths formed therein may be used.

Figure 2:
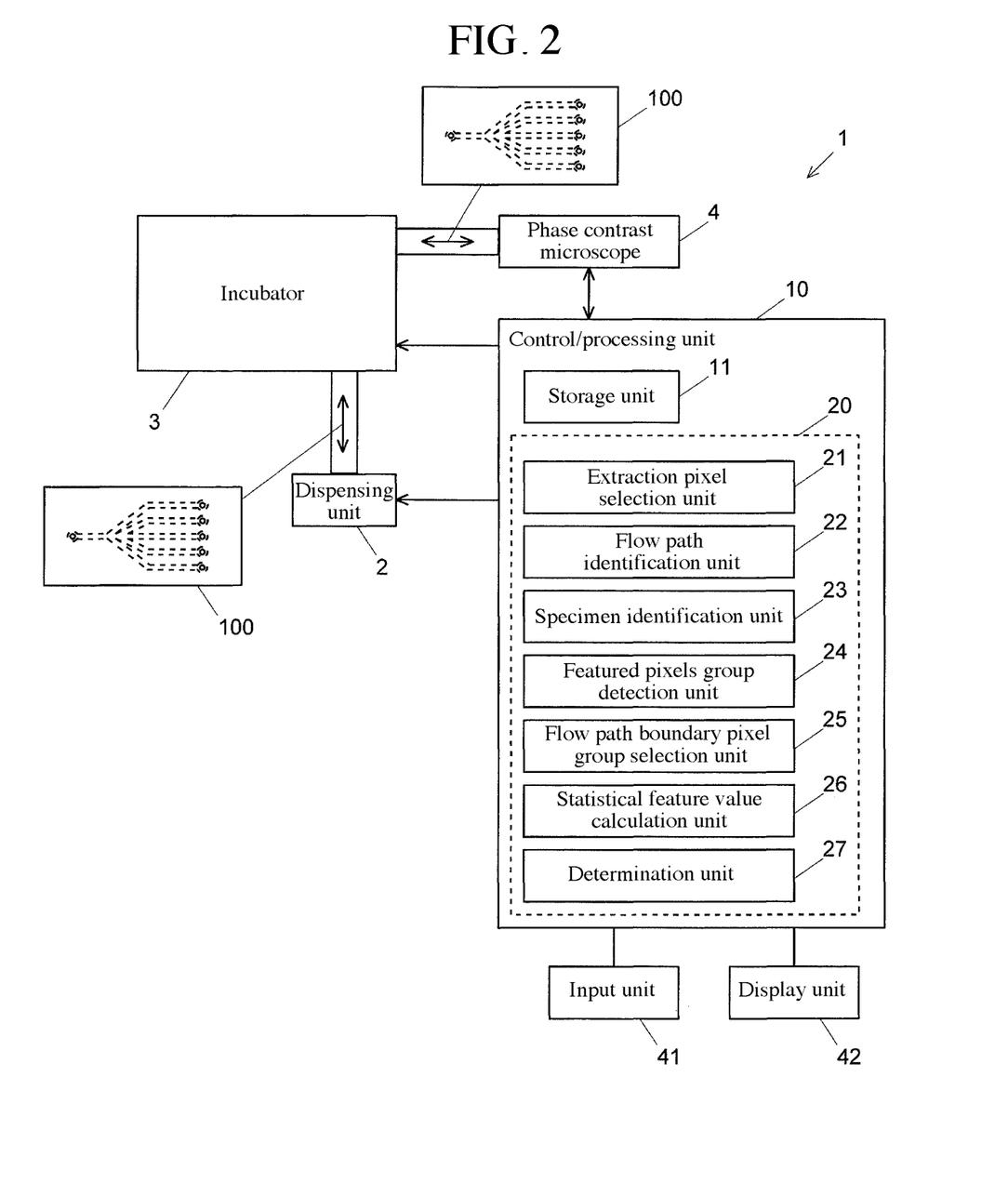
FIG. 2 is a configuration diagram of main parts of the microfluidic-device observation apparatus of Example 1.

FIG. 2 is a configuration diagram of a main part of the microfluidic-device observation apparatus 1 of Example 1. The microfluidic-device observation apparatus 1 of this example is roughly composed of a dispensing unit 2, an incubator 3, a phase contrast microscope 4 (imaging unit), and a control/processing unit 10. Between the dispensing unit 2 and the incubator 3, and between the incubator 2 and the phase contrast microscope 4, a device-transfer path and a transferring mechanism (not shown) are provided for transferring the microfluidic device 100 between the two devices in response to an instruction from the control/processing unit 10.

The control/processing unit 10 includes a function of controlling the operation of the dispensing unit 2, the incubator 3, and the phase contrast microscope 4 and a function of processing an image obtained by the phase contrast microscope 4. The control/processing unit 10 includes a storage unit 11, and further includes, as functional blocks, an extraction pixel selection unit 21, a flow path identification unit 22, a specimen identification unit 23, a feature pixel group detection unit 24, a flow path boundary pixel group selection unit 25, a statistical feature value calculation unit 26, and a determination unit 27. The entity of the control/processing unit 10 is a general computer. By executing the microfluidic-device observation program 20 by the processor, these functional blocks are embodied. Further, to the control/processing unit 10, an input unit 41 for an examiner to input information appropriately, and a display unit 42 for displaying an image or the like of the flow paths of the microfluidic device 100 are connected.

Template images of the microfluidic device 100 are stored in the storage unit 11. The template image of the microfluidic device 100 is used to identify the position of a flow path from the image obtained by imaging the microfluidic device 100 with the phase contrast microscope 4. In this example, only one type of microfluidic device 100 is used, but in a case where plural types of microfluidic devices are used, a template image is prepared for each type and stored in the storage unit 11.

One inlet port 101 and five air ports 102a to 102e are provided on the upper surface of the microfluidic device 100. A bacterial suspension introduction flow path 103 having one end immediately below the inlet port 101 is provided in the microfluidic device 100. The bacterial suspension introduction flow path 103 branches in the middle into five branched flow paths 103a to 103e each extending linearly to immediately below the air ports 102a to 102e, respectively. The five branched flow paths 103a to 103e are arranged parallel to each other in the vicinity of the air ports 102a to 102e. Note that FIG. 1 shows branched flow paths 103a to 103e in an easy-to-understand manner, and in an actual microfluidic device, the flow path width of the branched flow paths 103a to 103e is wider than that of the flow path spacing.

Next, the flow of the sensitivity test of target bacteria to an antimicrobial agent using the microfluidic-device observation apparatus 1 of this example will be described.

An examiner prepares antimicrobial solutions a to d including target bacteria at a predetermined ratio (e.g., defined by the number of target bacteria and the quantity of the culture medium) and antimicrobial solutions a to d including antimicrobial agents to be used for the test at differing concentrations and sets in the dispensing unit 2.

When the examiner instructs the start of the test through the input unit 41, a control signal instructing the start of the dispensing operation is transmitted from the control/processing unit 10 to the dispensing unit 2. In a case where there is a plurality of types of usable microfluidic devices, the examiner can identify the type of the microfluidic device 100 to be used for the examination.

In the dispensing unit 2, the antimicrobial solutions a to d are introduced into the branched flow paths 103a to 103d of the microfluidic device 100, respectively. Subsequently, the bacterial suspension containing the target bacteria is introduced into the bacterial suspension introduction flow path 103 through the inlet port 101. It should be noted that the antimicrobial solution is not introduced into the branched flow path 103e, and the number and size of the target bacteria in the branched flow path 103e are used as references for determining the susceptibility of the target bacteria to the antimicrobial solutions a to d introduced into other flow paths. The introduction amount of the bacterial suspension is determined in advance so as to reach the position of the antimicrobial agent fixed to the branched flow paths 103a to 103d. Since the air ports 102a to 102e for ventilation are formed at the ends of the branched flow paths 103a to 103e, the air in each of the branched flow paths 103a to 103e is discharged through the air ports in accordance with the inflow of the bacterial suspension, and the bacterial suspension flows into each of the branched flow paths 103a to 103e. In the branched flow paths 103a to 103d, the inflowed bacterial suspension comes into contact with the antimicrobial agent fixed to the wall surface of each flow path.

After introducing the antimicrobial solutions a to d and the bacterial suspension, the microfluidic device 100 is transferred to the incubator 3 and warmed to a predetermined temperature for a predetermined time to culture the target bacteria. After culturing for a predetermined time, the microfluidic device 100 is transferred from the incubator 3 to the phase contrast microscope 4. Hereinafter, referring to the flowchart of FIG. 3, the procedures for observing the target bacteria present in the flow paths of the microfluidic device in the microfluidic-device observation apparatus 1 of this example will be described below.

Figure 3:
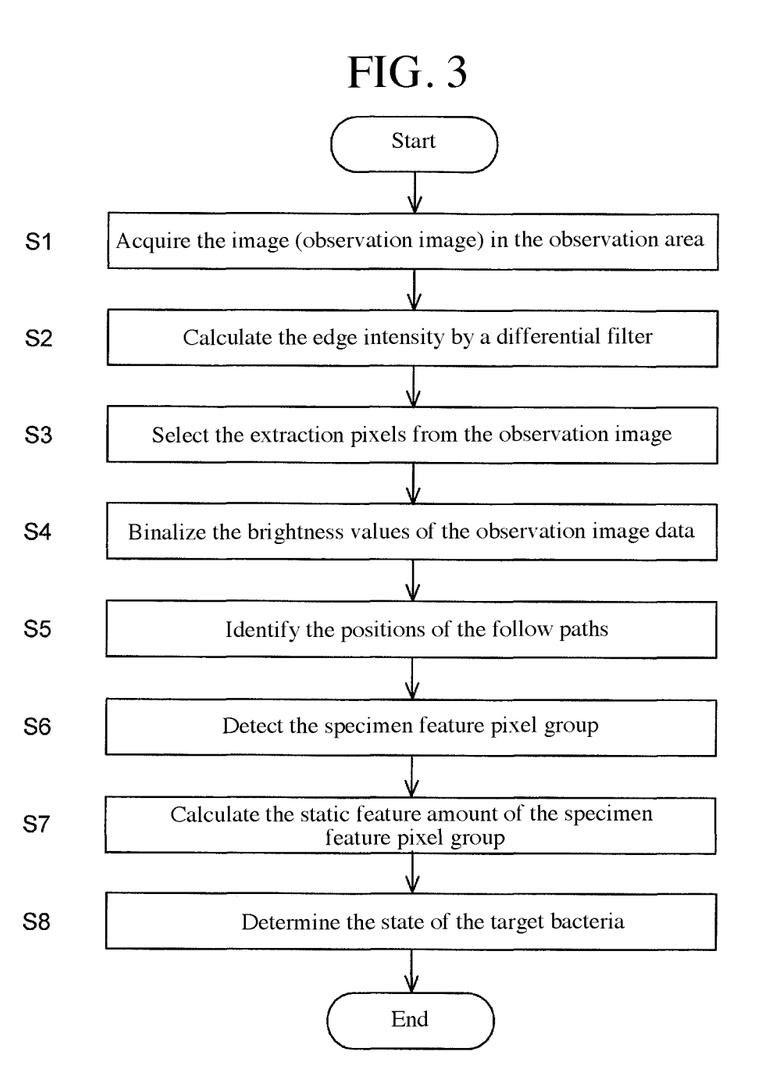
FIG. 3 is a flowchart for explaining procedures for observing a specimen present in flow paths of the microfluidic device of Example 1.

The microfluidic device 100 transferred to the phase contrast microscope 4 is held in a predetermined orientation at a predetermined imaging position. The phase contrast microscope 4 images the area of the microfluidic device 100 captured in the field of view. Of the entire microfluidic device 100, the area captured in the field of view of the phase contrast microscope 4 (corresponding to at least a part of the area of the microfluidic device 100) becomes the observation area 104, and the image (hereinafter, referred to as "observation image") of the observation area 104 is acquired by the phase contrast microscope 4 (Step S1). The phase contrast microscope 4 transmits the image data of the acquired observation area 104 to the control/processing unit 10. The image data received by the control/processing unit 10 is stored in the storage unit 11.

When the image data is stored in the storage unit 11, the extraction pixel selection unit 21 calculates the edge intensity (luminance value variations) in the image using a differential filter (Step S2). The image obtained by the phase contrast microscope 4 may be used as it is to perform the processing described later. However, by performing preprocessing using a differential filter, the processing described later can be performed with higher accuracy using the edge intensity in the image. As the differential filter, in addition to a first derivative filter, such as, e.g., a sobel filter, a prewitt filter, or a canny filter, a second derivative filter, such as, e.g., a laplacian filter, can be used. Instead of using a differential filter, various methods for detecting luminance changes included in the image data, such as, e.g., a morphology calculation, can be used.

Figure 4:
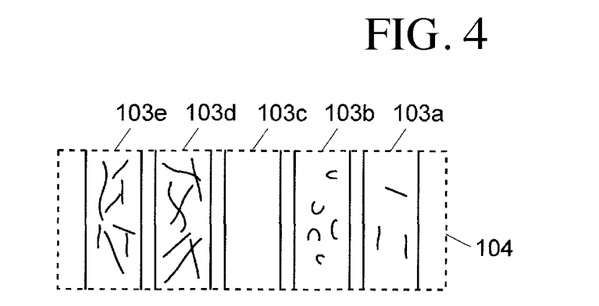
FIG. 4 is an example of an image obtained by binarizing the luminance values of the observation image data of Example 1.

The extraction pixel selection unit 21 selects pixels whose edge intensity value is equal to or greater than a predetermined value as extraction pixels (Step S3) for the image data from which the edge intensity was extracted by using the differential filter, and binarizes the image data by giving a value of 1 to the selected pixels and 0 to non-selected pixels (Step S4, see FIG. 4). Here, it is binarized by values of 0 and 1, but the binarization may be performed by using other values or codes. Further, here, regardless of the position in the pixel, the extraction pixels are selected by using the same predetermined value. However, a predetermined value corresponding to the magnitude of the luminance value of each pixel (e.g., a pixel having a value of the edge intensity equal to or greater than a predetermined ratio with respect to the luminance value of the target pixel is used as the extraction pixel) may be used. With this, even in cases where there is a bright portion (luminance value is large) and a dark portion (luminance value is small) in the image due to the environment at the time of imaging, it is possible to appropriately select the extraction pixels. Further, among the entire image, a different threshold may be used according to the dispersion of the luminance values in a predetermined range centered on the target pixel (e.g., a range of 9 pixels×9 pixels). Note that the size of the bacteria is small compared to the width and the length of the flow path, but in FIG. 4, the bacteria are shown larger than the actual one to show the presence of the target bacteria in an easy-to-understand manner.

There are roughly two processing methods after the binarization of the image data. When the examiner identifies the type of the microfluidic device 100 to be used for the test at the time of starting the test (or when only one type of microfluidic device 100 is available), the flow path identification unit 22 identifies the positions of the flow paths included in the observation image by template matching. First, this processing will be described.

The flow path identification unit 22 reads out a template image 110 of the microfluidic device 100 from the storage unit 11. As shown in (a) of FIG. 5, the template image 110 is an image in which hatching is applied to places other than the flow path.

Next, the flow path identification unit 22 superimposes the template image 110 on the observation image acquired by the phase contrast microscope 4, and identifies the position where the degree of coincidence between the boundaries of the flow paths included in the observation image and the boundaries of the flow paths of the template image 110 is the highest while shifting the relative positions of both images slightly. When the position where the degree of coincidence between the boundaries of the flow paths included in the observation image and the boundaries of the flow paths of the template image 110 is the highest is identified, the flow path identification unit 22 generates an image 104*a* (an image in which hatching is added to a portions other than the branched flow paths 103*a* to 103*e*) in which the template image is superimposed on the observation image, and identifies the image of the branched flow paths 103*a* to 103*e* (Step S5), as shown in (b) of FIG. 5. Then, the image data of each of the branched flow paths 103*a* to 103*e* is stored in the storage unit 11, and these images are displayed on the display unit 42.

Figure 5:
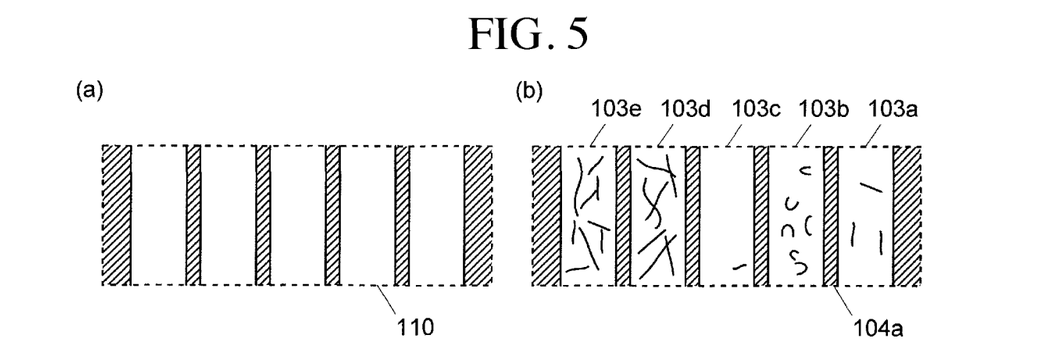
FIG. 5 is a diagram for explaining a template image used in Example 1.

Note that instead of using the above-described template image 110, it is also possible to extract the image of the branched flow paths 103*a* to 103*e* based on the degree of coincidence between the linear template filter and the image by using known structural information (for example, five linear flow paths are formed) relating to the flow paths of the microfluidic device 100. Alternatively, in a case where the microfluidic device 100 to be used is predetermined and the position to be set in the phase contrast microscope 4 is positioned with high accuracy, it is possible to automatically extract the area existing at a predetermined position of the observation image as the image of the branched flow paths 103*a* to 103*e* without using a template image or a template filter. Another method of identifying the flow paths is described below.

When the positions of the branched flow paths 103*a* to 103*e* in the observation image are identified in Step S5, the specimen identification unit 23 operates the feature pixel group detection unit 24 to identify the target bacteria present in each of the branched flow paths 103*a* to 103*e*. In this example, the specimen identification unit 23 and the feature pixel group detection unit 24 cooperate to detect the specimen-featured-pixels group (i.e., function as a specimen-featured-pixels detection unit in the present invention).

When identifying the specimen, the feature pixel group detection unit 24 detects a certain number or more of consecutive extraction pixels as a specimen-featured-pixels group from the binarized image of each of the branched flow paths 103*a* to 103*e* (Step S6). The predetermined number may be any number capable of separating the target bacteria present in the flow path and the noise, and may be, for example, the number of pixels (e.g., five pixels) corresponding to the minimum size assumed as a target bacterium. Since noise data is rarely continuously present in a large number of pixels, noise included in the binarized flow path image can be removed by this processing.

When the specimen-featured-pixels group is detected by the feature pixel group detection unit 24, the statistical feature value calculation unit 26 identifies the number of specimen-featured-pixels groups (the number of the target bacteria) present in each of the branched flow paths 103*a* to 103*e* and the arrangement of the pixels (the shape of the target bacteria) constituting each of the specimen-featured-pixels groups. With this, statistical feature values relating to the number and the shape of the specimen present in the branched flow paths 103*a* to 103*e* are acquired (Step S7). In case where there exists a plurality of specimen-featured-pixels groups in one flow path, the statistical feature value representing the average shape of the specimens is obtained by dividing the sum of the statistical feature values of the specimen-featured-pixels groups corresponding to the plurality of target bacteria by the number. The statistical feature value related to the shape of the target bacteria may be the area (or area ratio) of the target bacteria, the peripheral length of the target bacteria, the long-axis/short-axis length of the target bacteria, the linearity or the roundness of the target bacteria, and the like. The area ratio of the target bacteria can be obtained from the ratio of the number of pixels constituting the specimen-featured-pixels group to the number of pixels in the flow path. The peripheral length of the target bacteria can be obtained from the length of the outer periphery surrounding the specimen-featured-pixels group. The long-axis/short-axis length of the target bacteria can be obtained as the maximum/minimum value of the straight-line length of the rectangle surrounding the specimen-featured-pixels group. The linearity and the circularity of the target bacteria can be obtained from the aspect ratio of the shape of the specimen-featured-pixels group or a predetermined mathematical formula (for example, $4\pi \times area/(perimeter)^2$). Other known statistical values can be used appropriately as the statistical feature values. Although the average of the statistical feature values is obtained here, the median value, the mode value, and the like may be obtained in addition to the average value.

When the statistical feature values of the bacteria in each branched flow path 103a to 103e by the statistical feature value calculation unit 26, the determination unit 27 determines the state (the susceptibility to the antimicrobial solutions a to d including the antimicrobial agent at different concentrations) present in the flow paths from the statistical feature values of the target bacteria in the branched flow paths 103a to 103d in which the antimicrobial solutions a to d have been introduced at different concentrations, based on the statistical feature values of the target bacteria in the branched flow path 103e in which no antimicrobial agent has been introduced (Step S8). The image of the flow paths, the statistical feature value obtained from the image, and the determination result based on the statistical feature values are displayed on the display unit 42.

Note that the information on the form change of the target bacteria may be output. For example, it may be configured such that in a case where the shape (linearity, circularity, etc.) of the target bacteria in the branched flow paths 103a to 103d differs from the shape of the target bacteria in the branched flow path 103e, the change in the statistical feature value corresponding to the shape is displayed on the display unit 42. This makes it possible to obtain the information or the like about, for example, the presence or absence of the target bacteria denature due to the action of the antimicrobial agent.

Figure 6:
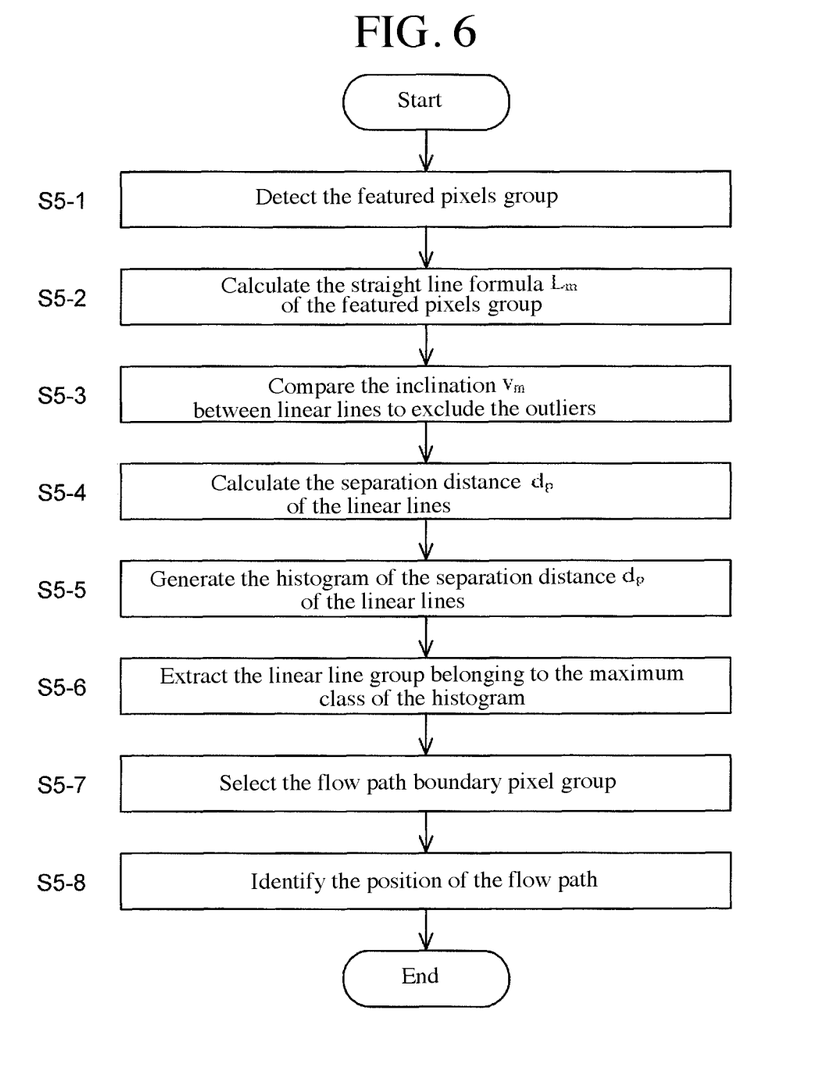
FIG. 6 is a flowchart for explaining one of the procedures for identifying a flow path position in the observation image of Example 1.

Another method of identifying the positions of the flow paths included in the observation image will be described with reference to the flowchart of FIG. 6.

In a case where there are several types of microfluidic devices capable of being used for examinations and the examiner has not identified the type of the microfluidic device, the flow path identification unit 22 sequentially operates the feature pixel group detection unit 24 and the flow path boundary pixel group selection unit 25 to extract the image of the flow paths. In the subsequent processing, flow path feature pixel groups are detected by the cooperation of the flow path identification unit 22 and the feature pixel group detection unit 24.

Among the extraction pixels selected by the extraction pixel selection unit 21, there are pixels located at the boundaries of the flow paths, pixels at a position where the target bacteria exist, pixels at a position where noise occurred, and the like. Therefore, the feature pixel group detection unit 24 detects, as a flow path feature pixel group, a certain number or more of extraction pixels arranged continuously in a linear pattern from the binarized image data (Step S5-1). Here, the predetermined number is a number capable of estimating the shape of the flow path feature pixel group from the positions of the pixels of the predetermined number. The predetermined number differs depending on the shape of the flow paths. In this embodiment, since the straight-line formula representing the flow path feature pixel group is obtained based on the positions (coordinates) of the pixels constituting the flow path feature pixel group, it is only necessary to include at least two extraction pixels, but if the predetermined number is too small, the accuracy of the straight-line formula is poor. On the other hand, as the predetermined number increases, the straight-line formula representing the flow path feature pixel group can be obtained with higher accuracy. However, if the predetermined number is too large, when the contrast does not appear in a part of the pixels located at the boundary of the flow paths and the pixels are not selected as the extraction pixels (that is, when the number of consecutive extraction pixels is small), the extraction pixels located at the boundaries of the flow paths are not detected as the flow path feature pixel group. In consideration of the above, it is preferable that the predetermined number be about the number of pixels corresponding to 10% of the image size (the short diameter in the case of a rectangular image or the diameter in the case of a circular image).

Next, the flow path boundary pixel group selection unit 25 assigns a number m (m is an integer equal to or greater than 1 and equal to or less than n) to the n pieces of flow path feature pixel groups detected by the feature pixel group detection unit 24, and obtains a straight-line formula $L_m$ representing each flow path feature pixel group (Step S5-2). The straight-line formula $L_m$ representing the flow path feature pixel group means an approximated straight line based on the coordinates of a plurality of extraction pixels constituting a flow path feature pixel group. In this example, the Hough transform is used to obtain the straight-line formula $L_m$ representing each flow path feature pixel group.

The Hough transform is one of techniques used to extract features of an image in the field of image processing. In the Hough transform, a straight-line formula is expressed on a two-dimensional plane (x-y plane) by a distance r from an origin to a normal line and an angle θ formed by the normal line and the x-axis. In the Hough transform, a straight-line formula represented by the following Formula (1) is used.

$$R = x \cos \theta + y \sin \theta \tag{1}$$

First, a straight-line formula using Formula (1) is obtained for one of the extraction pixels constituting the flow path feature pixel group. At this stage, only one coordinate value is identified. Therefore, the straight-line formula is not uniquely determined, and therefore it becomes a function of r and θ. For each of the extraction pixels constituting the flow path feature pixel group, a function of r and θ is obtained using the coordinates of the extraction pixels. Then, a function of r and θ obtained by the number of extraction pixels is projected into a Hough space with these as a two axis, and the value of r and θ with a large number of projections (the highest degree of coincidence) is obtained. With this, a straight-line formula representing the flow path feature pixel group is determined. In a case where the extraction pixels constituting the flow path feature pixel group are positioned on a straight line, the functions of r and θ obtained for each of the extraction pixels intersect at one point, and the straight line can be strictly determined by the values of r and θ corresponding to the intersection. However, in the actual image, since the flow path feature pixel group spans a plurality of pixels in the width direction, or is partially stepped, the extraction pixels are rarely positioned completely on a straight line. Therefore, the straight-line formula corresponding to the flow path feature pixel group is determined by the values of r and θ with a large number of projections in the Hough space. Thus, the following Formula (2) is obtained as a straight-line formula $L_m$ for the $m^{th}$ flow path feature pixel group.

$$a_m x + b_m y = 1 (a_m, b_m \text{ is a factor}) \tag{2}$$

In this example, the straight-line formula $L_m$ corresponding to each flow path feature pixel group is obtained by the Hough transform, but the straight-line formula $L_m$ can also be obtained by other methods. For example, a least squares method may be used to determine approximated straight lines for the coordinates of each of the extraction pixels constituting the flow path feature pixel group.

Next, the flow path boundary pixel group selection unit 25 determines the inclination of the straight-line formula $L_m$ obtained for each flow path feature pixel group. The unit vector $v_m$ representing the inclination of the straight-line formula $L_m$ represented by the above-described Formula (2) is represented by the following Formula (3).

$$v_m = (-b_m/l_m, a_m/l_m) \text{ (where, } l_m = (a_m^2 + b_m^2)^{1/2}) \quad (3)$$

After the inclination $v_m$ is obtained for all straight-line formulas $L_m$, the median $V_{ctr}$ of the inclination is obtained. Then, flow path feature pixel groups (outliers) corresponding to a straight line with an inclination that does not satisfy the following Formula (4) are excluded from the processing targets (Step S5-3).

$$|<v_m \cdot v_{ctr}>| \geq \alpha \text{ (}\alpha \text{ is a value equal to or greater than 0 and less than 1)} \quad (4)$$

Formula (4) is the inner product of the inclination $v_m$ of the straight-line formula Lm corresponding to each flow path feature pixel group and all of the median $V_{ctr}$. Also, $\alpha$ is a real number of equal to 0 or more and less than 1. That is, Formula (4) means that the parallelism with respect to the straight line having the inclination of the mean value $V_{ctr}$ is equal to or more than a predetermined value (inclination $V_m$ of the straight-line formula $L_m$ is close to the inclination of the other straight-line formulas). In the microfluidic device 100 of this embodiment, since the plurality of branched flow paths 103a to 103e is formed in parallel in the observation area 104, the straight lines corresponding to the flow path feature pixel groups positioned at the boundaries of the flow paths should be parallel to each other. Therefore, by excluding the flow path feature pixel group corresponding to a straight line having an inclination that does not satisfy the above-described Formula (4) from the processing target, it is possible to exclude the flow path feature pixel group (corresponding to the position of the target cell or the like) that is considered not to be the boundary of the flow path.

Although the median $V_{ctr}$ of the straight-line formula $L_m$ corresponding to each flow path feature pixel group is used here, it is not always necessary to use a median value. A suitable one can be used, such as, e.g., the mean value of the inclination $V_m$ of the straight-line formula $L_m$ corresponding to each flow path feature pixel group, or the mean value obtained by obtaining the distribution of the inclination $V_m$ of the straight-line formula $L_m$ corresponding to each flow path feature pixel group and excluding the predetermined number of inclinations corresponding to the end of the distribution. In a case where it is possible to estimate the approximate inclination of the straight line (the inclination of the flow path within the observation image) corresponding to the flow path border, the estimated inclination may also be used.

For k (k≤n) pieces of straight-line formulas $L_p$ remaining after the above-described processing (p is an integer between 1 and k), the distance from each straight line to another straight line adjacent in a particular direction (e.g., the positive direction of the x-axis) is obtained (Step S5-4). Since these straight lines $L_p$ are not strictly parallel to each other, the separation distance $d_p$ of the straight line is defined as follows.

Figure 7:
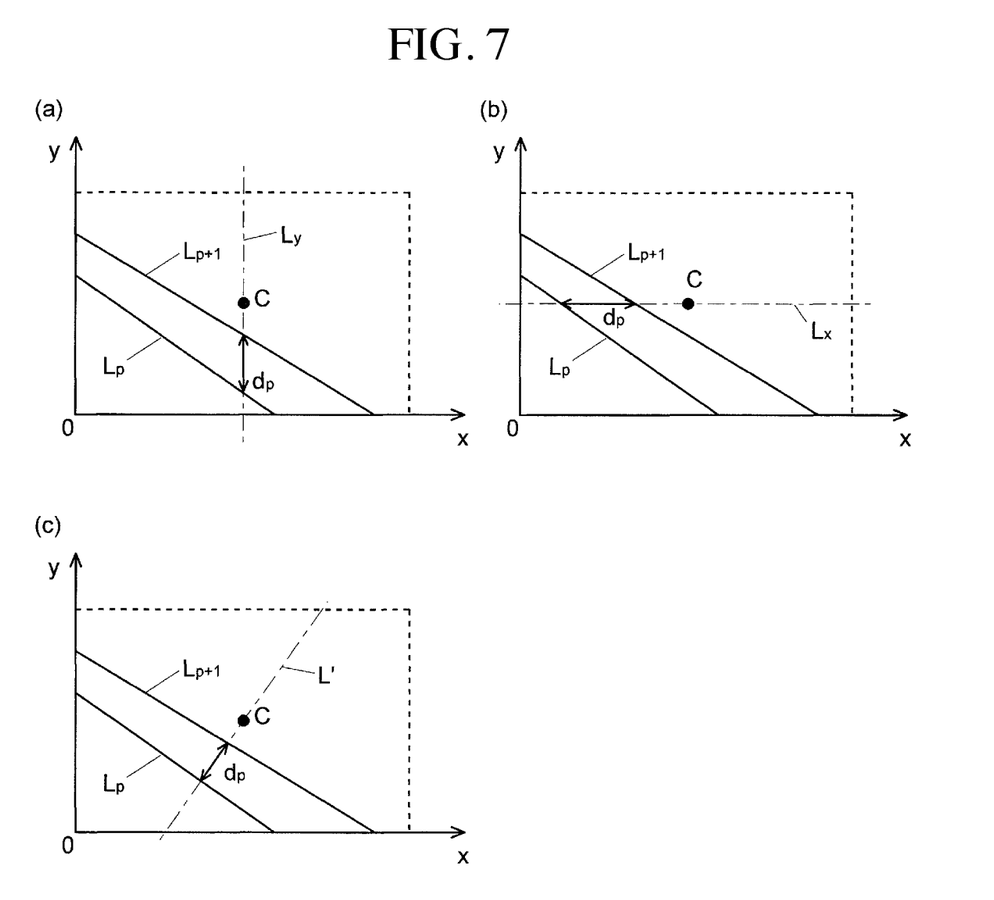
FIG. 7 is a diagram for explaining a method of determining a separation distance of straight lines in one of the procedures for identifying the flow path position in the observation image in Example 1.

In this embodiment, as shown in (a) of FIG. 7, for each of the straight lines represented by a straight-line formula $L_p$ of interest and the adjacent straight-line formula $L_{p+1}$, the intersection points with the straight line (straight-line Formula $L_y$) passing through the center C of the observation image and parallel to the y-axis. Then, the distance between these intersection points is defined as the separation distance $d_p$ between the two straight lines. As shown in (b) of FIG. 7, for each of the straight lines represented by the straight-line formula $L_p$ of interest and the adjacent straight-line formula $L_{p+1}$, the intersection points with a straight line (straight line formula $L_x$) passing through the center C of the observation image and parallel to the x-axis are obtained, and the distance between these intersection points may be defined as the separation distance $d_p$ between the two straight lines. Further, as shown in (c) of FIG. 7, for each of the straight lines represented by the straight-line formula $L_p$ of interest and the adjacent straight-line formula $L_{p+1}$, the intersection points with the normal line formula L' of the straight-line formula $L_p$ passing through the center C of the observation image is obtained, and the distance between these intersection points may be defined as the separation distance $d_p$ between the two straight lines.

Next, histograms are generated for the separation distances $d_p$ of the straight lines obtained for each of the k–1 pieces of the straight lines with predetermined class widths (Step S5-5). Note that the flow path width and the flow path spacing of the branched flow paths 103a to 103e formed in the microfluidic device 100 of this example are both constant. Thus, in the produced histograms, the separation distance $d_p$ corresponding to the flow path width should be the greatest, and then the separation distance $d_p$ corresponding to the flow path spacing should be the next greatest. Therefore, for each of the k–1 pieces of straight lines, it is determined whether or not the separation distances $d_p$ relating to the straight lines are included in the largest class.

In the microfluidic device 100 of this example, five branched flow paths lines 103a to 103e are formed in parallel to each other. Therefore, ideally, as shown in (a) of FIG. 8, four pieces of data exist at the position corresponding to the distance between flow paths, five pieces of data exist at the position corresponding to the flow path width, and no data exists at other positions. When such a histogram is obtained, it is determined that the separation distance $d_p$ obtained for the five straight lines is included in the largest class. With respect to the one determined to be included in the largest class, a pixel group (flow path boundary pixel group) constituting the boundary of the flow path may be selected by extracting a set of the straight line $L_p$ corresponding to the largest class and the adjacent straight line $L_{p+1}$.

Figure 8:
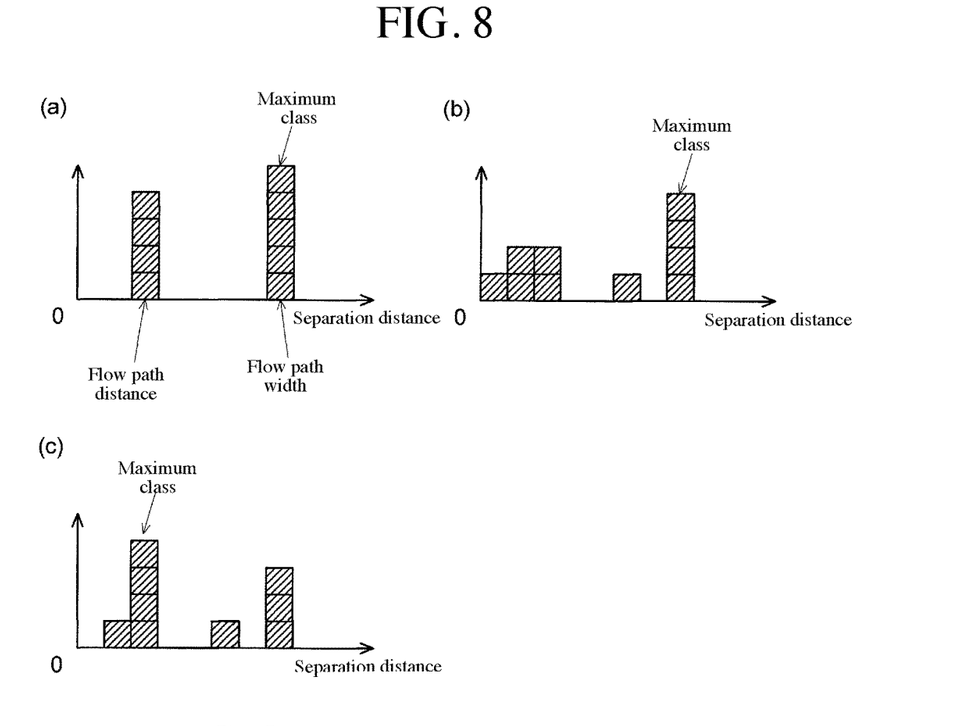
FIG. 8 is an example of a histogram generated in one of the procedures for identifying the flow path position in the observation image in Example 1.

However, in actuality, even after each of the above-described processing, a straight line other than the straight line constituting the boundary of the flow paths (a straight line derived from the target bacteria or a straight line derived from noise) may still be included in some cases. In this case, for example, a histogram as shown in (b) of FIG. 8 or (c) of FIG. 8 is obtained. Even in such a case, the straight lines constituting the boundaries of the flow paths are positioned at regular intervals corresponding to the flow path width and the flow path spacing, while the other straight lines are positioned at random. Therefore, when the maximum class in the histogram is selected, either the flow path width ((b) of FIG. 8) or the flow path spacing ((c) of FIG. 8) is selected. Therefore, by extracting a set of a straight line $L_p$ corresponding to the straight line and the adjacent straight line $L_{p+1}$ (Step S5-6), pixel groups (flow path boundary pixel groups) constituting the flow path boundaries can be selected (Step S5-7).

Figure 9:
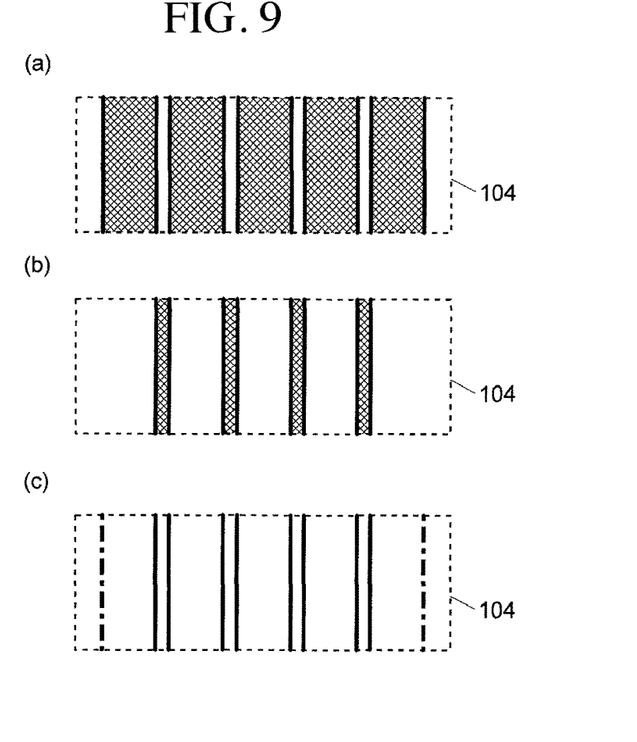
FIG. 9 is a diagram for explaining a method of identifying a flow path from an observation image in one of the procedures for identifying the flow path position in the observation image in Example 1.

When the flow path boundary pixel group is selected by the above-described processing, the positions of the borders of the flow paths in the observation image are known as shown in (a) of FIG. 9 or (b) of FIG. 9. In the state shown in (a) of FIG. 9 (the state obtained from the histogram of (a) of FIG. 8 or (b) of FIG. 8), a pair of two straight lines from the end of the image may be used as a flow path in the region (hatched portion) sandwiched between them. On the other hand, in the state shown in (b) of FIG. 9 (the state obtained from the histogram of (c) FIG. 8), when two straight lines are formed as one set from the end of the image, the region (hatched portion) sandwiched between them is not a flow path.

Therefore, after the positions of the boundaries of the flow paths in the observation image are determined, the flow path width in the case where two lines from the end are selected as one set and the region sandwiched therebetween is considered as a flow path and the flow path width in the case where two lines are selected in order from the second straight line from the end and the region sandwiched therebetween is considered as a flow path compared to determine which of the flow path widths is wider. As described above, in FIG. 1, the flow path width is shown to be narrow for easy understanding of the flow path, but in the microfluidic device actually used, the flow path width is wider than the flow path spacing. Therefore, as a result of the above-described comparison, the flow path determined to be wider is determined as a flow path. When it is determined that the latter case in which the flow path width (in the case where two pixels are selected as a set in order from the second straight line from the end) is larger, the flow path boundary pixel groups positioned in a straight line remain one by one at both ends of the image. Whether or not a flow path having the same width as that of the other flow path can be added outside each of the straight lines left at both ends (that is, whether or not a space corresponding to the flow path width remains outside the straight line) is determined. When it is possible, a straight line corresponding to the boundary of the flow path (indicated by a dashed line in (c) FIG. 9) is added. With this, a flow path is added.

When the positions of the flow paths in the observation image are determined by the above-described processing, the flow path identification unit 22 identifies the position of each of the flow paths 103a to 103e included in the observation image (Step S5, Step S5-8). The image data of the flow paths 103a to 103e are stored in the storage unit 11, and the image data is displayed on the display unit 42. At this time, the image of the positions of the identified flow paths may be extracted as they are, but in order to prevent the contrast of the boundaries of the flow paths from affecting the image of the flow paths and erroneously recognizing the contrast as target bacteria, an area inside the determined position of the flow path by a predetermined number of pixels may be extracted as the image of the flow path.

Figure 10:
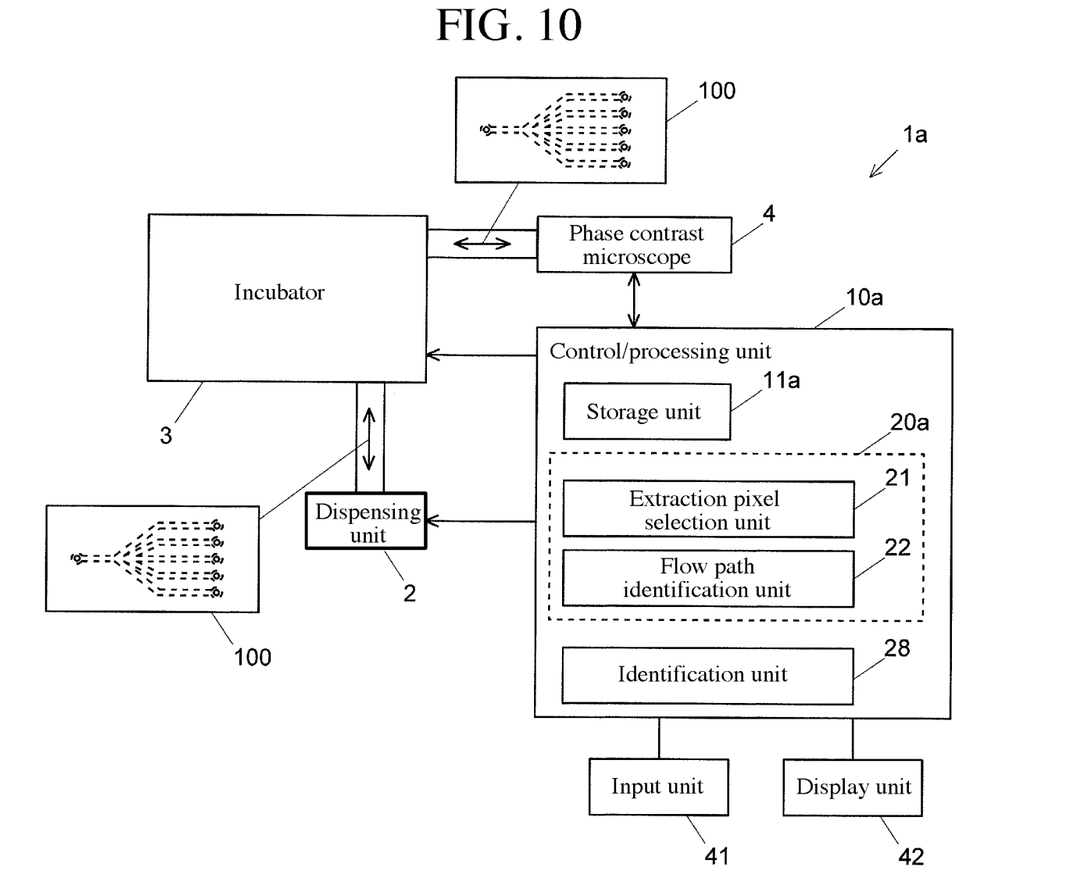
FIG. 10 is a configuration diagram of main parts of a microfluidic-device observation apparatus of Example 2.

Next, a microfluidic-device observation apparatus 1a of Example 2 will be described. FIG. 10 is a configuration diagram of a main part of a microfluidic-device observation apparatus 1a of this example. The same constituent elements as those of the microfluidic-device observation apparatus 1 of Example 1 are denoted by the same reference numerals, and the descriptions thereof will be omitted.

The microfluidic-device observation apparatus 1a of Example 2 differs from the microfluidic-device observation apparatus 1 of Example 1 in part of the configuration of the control/processing unit. Similar to the control/processing unit 10 of Example 1, the control/processing unit 10a has a function of controlling the operations of the dispensing unit 2, the incubator 3, and the phase contrast microscope 4, and a function of processing an image obtained by the phase contrast microscope 4. The control/processing unit 10a is provided with a storage unit 11a, and is also provided with, as functional blocks, an extraction pixel selection unit 21 and a flow path identification unit 22. Further, an identification unit 28 constructed by machine learning, which will be described later, is installed. The entity of the control/processing unit 10a is a general computer, and the above-mentioned functional blocks are realized by executing the microfluidic-device observation program 20a by the processor. To the control/processing unit 10a, an input unit 41 for an examiner to input information as appropriate and a display unit 42 for displaying an image or the like of the flow path of the microfluidic device 100 are connected.

The storage unit 11a stores the template image 110 described in Example 1 and a number of specimen referenced images. The specimen reference image is an image obtained by imaging target bacteria, which is the same specimen as this example, in which antimicrobial agents of various kinds are applied at various concentrations. Each of these images has been analyzed, and statistical feature values relating to the number and shape of target bacteria included in each image are identified in advance. In addition, the specimen reference image includes not only an image of a target bacterium having a normal shape but also an image whose shape has been modified by an antimicrobial agent, and the statistical feature values are required for the image.

The microfluidic-device observation apparatus 1a of Example 2 is characterized in the processing in which it calculates the statistical feature value of the target bacteria present in the flow path and the state of the target bacteria is determined. In Example 2, the identification unit 28 is generated by machine learning using a large number of specimen reference images stored in the storage unit 11 as training data. For such a method of machine learning, a method, such as, e.g., deep learning, support vector machine (SVM: Support Vector Machine), and random forest techniques, has been proposed.

In the microfluidic-device observation apparatus 1a of Example 2, prior to starting the examination of the target bacteria, the identification unit 28 for identifying the number and the shape of the target bacteria from the input image is constructed by machine learning using the image of the flow paths of the microfluidic device 100 and the statistical feature values of the target bacteria corresponding to the image as training data.

Also in Example 2, the processing of imaging the microfluidic device 100 with the phase contrast microscope 4, acquiring the edge intensity by processing the image data by a differential filter, and binarizing the image data is in the same manner as the processing in the microfluidic-device observation apparatus 1 of Example 1. Further, the processing of identifying the positions of the flow paths in the observation image uses any of the methods described in Example 1.

When the position of each of the branched flow paths 103a to 103e included in the observation image is identified by the flow path identification unit 22, the image data of each of the branched flow paths 103a to 103d is input to the identification unit 28. The identification unit 28 identifies the number and shape (e.g., linearity, circularity) of the specimens included in each of the input images of the branched flow paths 103a to 103e, and outputs them as the statistical feature values of the target bacteria. When a plurality of target bacteria is present in the branched flow paths 103a to 103e, the average of the statistical feature values of the plurality of target bacteria is output. As the statistical feature values, in addition to the linearity and the circularity, the area (or the area ratio) of the target bacterium, the surrounding length of the target bacterium, the long-axis/short-axis length of the target bacterium, and other known statistical quantities can be used. When these statistical feature values are used, the identification unit 28 may be constructed by machine learning for outputting the corresponding statistical feature values in accordance with the input of the image of the flow paths containing the target bacteria. Although the average of the statistical feature values is obtained here, the median value, the mode value, and the like may be obtained in addition to the average value.

The identification unit 28 obtains the average of the statistical feature values representing the numbers or the shapes of the target bacteria to determine their status (the susceptibility to the antimicrobial solutions a to d containing the antimicrobial agent at different concentrations) from the statistical feature values of the target bacteria in the branched flow paths 103a to 103d in which the antimicrobial solutions a to d different in the concentration have been introduced respectively, in the same manner as in Example 1, relative to the statistical feature values of the target bacteria in the branched flow path 103e in which not antimicrobial solution has been introduced. The image of the flow paths, the statistical feature values obtained from the image, and the determination result based on the statistical feature values are displayed on the display unit 42.

All of the above Examples are merely examples, and can be appropriately changed in accordance with the gist of the present invention. In the above-described Examples, the case in which the examination of the sensitivity of the target bacteria to the antimicrobial agent has been described, but the same microfluidic-device observation apparatus as described above can be used in examinations for other purposes.

In the above-described Examples, the method of detecting the boundaries of the flow paths and extracting the feature pixels of the bacteria by the same method has been described, but they may be performed by different methods. For example, in cases where the detection of the boundaries of the flow paths is performed by template matching, the extraction of the feature pixel of the bacteria may be performed by, for example, machine learning, so that the shape (including information such as the area) can be detected.

In the above-described Examples, the case in which five straight branched flow paths 103a to 103e are formed in the microfluidic device 100 has been described as an example, but the number of flow paths may be appropriately changed in accordance with the number (type of the concentration) of the antimicrobial solution used for the examination. The shape of the flow path is not limited to a straight line, and may be a curved line. The curved shape may be, for example, an arc shape (including an elliptical arc shape) or an S-shape (meandering shape). Even if the flow path shape is curved, the Hough transform described in this specification can be applied. In particular, when the flow path shape is a circular arc shape or an elliptical arc shape, the shape of the feature pixel group may be obtained by a mathematical formula representing a circle or an ellipse instead of the Hough transform in the above-described Examples, and the parallelism of the curve may be used instead of the parallelism of the straight line in the above-described Example. For example, for a certain curve, the concept of a parallel curve defined as a curve at a constant distance from each point on the curve in the normal direction can be used.

In both Examples 1 and 2, a phase contrast microscope is used as the imaging unit, but the type of imaging unit is not limited as long as it can acquire an image in which contrast appear at the boundaries of the flow paths formed in the microfluidic device. For example, an optical microscope, an optical camera, or a differential interference microscope can be used.

In the processing relating to identifying the positions of the flow paths described in Example 1 described above, after the positions of the flow paths in the observation image are determined, the flow path is determined by comparing the flow path width in the case where two flow paths are selected as one set from the end of the image and the region sandwiched between the two flow paths is selected in order from the second straight line from the end, and which of the flow path widths in the case where the region sandwiched between the two flow paths is wider is determined. However, the image in which the positions of the flow paths in the observation image is determined is displayed on the display unit 42, and the examiner may select which of them is flow paths by the operation through the input unit 41. Alternatively, it may be configured such that in a case where the flow path is determined without performing the above-described comparison, and an image of the flow paths extracted by the flow path identification unit 22 is displayed on the display unit 42, and the examiner has determined that this is not the flow path, an inversion operation (an operation of having the flow path identification unit 22 extract the image by using an area sandwiched between two straight lines different from the set of straight lines used as the boundary constituting the flow path) is instructed.

In addition, in the above-described Example 2, it is configured such that the observation image in which the positions of the flow paths are identified is input to the identification unit 28. However, it may be configured such that the image data of the microfluidic device 100 (the image data in which the positions of the flow paths are not identified) is input as it is to the identification unit 28 and the positions of the flow paths is identified by the identification unit 28. In this case, the identification unit 28 may be configured by machine learning using the image data of the microfluidic device in which various numbers and shape of the flow paths are formed in which the positions of the flow paths have been identified, as training data.

DESCRIPTION OF SYMBOLS 1, 1a: Microfluidic-device observation apparatus
2: Dispensing unit
3: Incubator
4: Phase contrast microscope
10a: Control/processing unit
10, 10a: Control/processing unit
11, 11a: Storage unit
110: Template image
20, 20a: Microfluidic-device observation program
21: Extraction pixel selection unit
22: Flow path identification unit
23: Specimen identification unit
24: Feature pixel group detection unit
25: Flow path boundary pixel group selection unit
26: Statistical feature value calculation unit
27: Determination unit
28: Identification unit
41: Input unit
42: Display unit
100: Microfluidic device
101: Inlet port
102a to 102e: Air port

103: Bacterial suspension introduction flow path
103a to 103e: Branched flow path
104: Observation area
110: Template image

The invention claimed is:

1. A microfluidic-device observation apparatus for observing a specimen present in a plurality of flow paths arranged in a microfluidic device, comprising:
   an imaging unit configured to acquire an image of the microfluidic device, the imaging unit being a camera or a microscope; and
   a computer configured by a program comprising
      a flow path identification unit configured to locate the plurality of flow paths included in the image; and
      an identification unit constructed by machine learning using the image of the microfluidic device in which the specimen is present in the flow paths and the number and/or the shape of the specimen in the image as training data, the identification unit being configured to identify the number and/or the shape of the specimen present in each of the plurality of identified flow paths when the acquired image is input.

2. The microfluidic-device observation apparatus as recited in claim 1,
   wherein the identification unit obtains a representative value of a statistical feature value related to the number and/or the shape of the plurality of the specimens in a case where the plurality of specimens is present in one flow path.

3. The microfluidic-device observation apparatus as recited in claim 1,
   wherein the identification unit determines a state of the specimen present in each flow path based on the number and/or the shape of the identified specimen.

4. The microfluidic device-observation apparatus as recited in claim 1,
   wherein the flow path identification unit specifies the positions of the plurality of flow paths included in the image and identifies an area sandwiched by adjacent boundaries as the flow path.

5. The microfluidic device-observation apparatus as recited in claim 1,
   wherein in at least a part of a region of the microfluidic device, the plurality of flow paths have a same width, the plurality of flow paths being arranged in parallel to each other, and
   wherein the flow path identification unit includes:
      a flow path feature pixel group detection unit configured to detect a plurality of extraction pixel groups in which a mutual parallelism is equal to or greater than a predetermined parallelism from a plurality of extraction pixel groups each comprising a prescribed number or more of the extraction pixels arranged continuously in a line each as a flow path feature pixel group;
      a flow path boundary pixel group selection unit configured to select a set of feature pixel groups in which a separation distance corresponds to a width of the flow path as a flow path boundary pixel group from the plurality of flow path feature pixel groups; and
      a flow path image extraction unit configured to extract an image of each flow path by identifying a position of a boundary of the one or a plurality of flow paths based on the position of the low path boundary pixel group in the image.

6. The microfluidic-device observation apparatus as recited in claim 5,
   wherein the flow path is formed in a straight line, and
   wherein the flow path feature pixel group detection unit obtains an approximated straight line corresponding to the positions of the pixels constituting the extraction pixel group for each of the extraction pixel groups, and detects a group in which a difference between an inclination of the approximated straight line and an inclination of the other approximated curves is equal to or less than a predetermined inclination, as a feature pixel group.

7. The microfluidic-device observation apparatus as claimed in claim 6,
   wherein the flow path feature pixel group detection unit obtains the approximated straight line by a Hough transform.

8. The microfluidic-device observation apparatus as recited in claim 5,
   wherein a plurality of the flow paths is are arranged in parallel to each other, and
   wherein the flow path boundary pixel group selection unit selects a group in which the separation distance between adjacent two of the flow path feature pixel groups is equal as the flow path boundary pixel group.

9. The microfluidic-device observation apparatus as claimed in claim 8,
   wherein the flow path boundary pixel group selection unit generates a histogram related to the separation distance and selects a group belonging to a largest class as the flow path boundary pixel group.

* * * * *